(12) United States Patent
Kusumoto et al.

(10) Patent No.: US 9,255,055 B2
(45) Date of Patent: Feb. 9, 2016

(54) METHOD FOR PRODUCING COMPOUND

(71) Applicant: DIC CORPORATION, Tokyo (JP)

(72) Inventors: Tetsuo Kusumoto, Saitama (JP); Takashi Matsumoto, Saitama (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/371,365

(22) PCT Filed: Apr. 5, 2013

(86) PCT No.: PCT/JP2013/060453
§ 371 (c)(1),
(2) Date: Jul. 9, 2014

(87) PCT Pub. No.: WO2014/162588
PCT Pub. Date: Oct. 9, 2014

(65) Prior Publication Data
US 2015/0197471 A1  Jul. 16, 2015

(51) Int. Cl.
- *C07C 41/40* (2006.01)
- *C07C 43/225* (2006.01)
- *C09K 19/20* (2006.01)
- *C09K 19/30* (2006.01)
- *C09K 19/04* (2006.01)

(52) U.S. Cl.
CPC ............... *C07C 41/40* (2013.01); *C07C 43/225* (2013.01); *C09K 19/20* (2013.01); *C09K 19/3066* (2013.01); *C09K 2019/0448* (2013.01); *C09K 2019/0466* (2013.01); *C09K 2019/301* (2013.01); *C09K 2019/3077* (2013.01)

(58) Field of Classification Search
CPC ...................................... C07C 41/40
See application file for complete search history.

(56) References Cited

U.S. PATENT DOCUMENTS

| | | | |
|---|---|---|---|
| 6,007,740 A | 12/1999 | Andou et al. | |
| 6,787,062 B2 * | 9/2004 | Kirsch et al. | 252/299.63 |
| 6,858,267 B2 * | 2/2005 | Manabe et al. | 428/1.1 |
| 2002/0120168 A1 | 8/2002 | Kondo et al. | |
| 2003/0069433 A1 | 4/2003 | Kirsch et al. | |

FOREIGN PATENT DOCUMENTS

| | | |
|---|---|---|
| JP | 58-1774 A | 1/1983 |
| JP | 62-210420 A | 9/1987 |
| JP | 10-204016 A | 8/1998 |
| JP | 2002-53513 A | 2/2002 |
| JP | 2003-213261 A | 7/2003 |
| JP | 2003-525286 A | 8/2003 |
| JP | 2006-241040 A | 9/2006 |
| JP | 2011-105687 A | 6/2011 |

OTHER PUBLICATIONS

International Search Report dated Jul. 2, 2013 issued in corresponding application No. PCT/JP2013/060453.

* cited by examiner

*Primary Examiner* — Brian J Davis
(74) *Attorney, Agent, or Firm* — Westerman, Hattori, Daniels & Adrian, LLP

(57) ABSTRACT

In sequential steps including preparing a solution of a compound having —$CF_2O$— as a linking group, bringing the solution into contact with a purifying agent or not bringing the solution into contact with a purifying agent, subsequently performing crystallization from the obtained solution for crystallization to precipitate a crystal, collecting the crystal by filtration, and drying the crystal, steps from the initiation of the crystallization step to the end of the drying step are performed in an atmosphere having an oxygen concentration of 3% by volume or less.

14 Claims, No Drawings

METHOD FOR PRODUCING COMPOUND

TECHNICAL FIELD

The present invention relates to a method for producing a compound.

BACKGROUND ART

Liquid crystal display devices have come to be used in wide-ranging applications including consumer products such as liquid crystal televisions, cellular phones, and personal computers and industrial equipment. Such products have a relatively long life span of several years to 10 or more years. In order to allow normal operation of display devices for the life span, liquid crystal materials used for liquid crystal display devices are required to have high stability. A representative index of stability of liquid crystal materials is resistivity. In order to allow normal operation of liquid crystal display devices, liquid crystal materials used for the liquid crystal display devices need to have a sufficiently high resistivity and deterioration over time also needs to be suppressed.

There are other various requests for liquid crystal materials, for example, liquid crystal materials that allow higher response speed and higher contrast. Such properties cannot be achieved by a single compound and hence a plurality of liquid crystal compounds are mixed to provide liquid crystal compositions that meet the requests. Accordingly, in order to obtain liquid crystal materials having high stability, liquid crystal compounds constituting the liquid crystal materials need to have high stability.

The stability of liquid crystal compounds is effectively enhanced by increasing the purity through removal of impurities or removing water, organic ions, inorganic ions, and the like from liquid crystal materials. In general, this is performed by a process of bringing compounds into contact with silica gel or alumina or a process of purifying compounds by recrystallization (Patent Literatures 1 and 2).

However, among compounds constituting liquid crystal materials, compounds having —$CF_2O$— as a linking group have low chemical stability and may undergo, for example, oxidation with oxygen, hydrolysis with water, or dissociation of fluorine atoms. This results in a decrease in the purity, which may also cause a decrease in the resistivity. For this reason, in spite of purification of compounds by the above-described processes or the like, the compounds undergo oxidation reaction or the like upon contact with oxygen, water, or the like during the purification treatment; and the resultant compounds do not satisfy the required purity or resistivity, which has been problematic. There has been a strong demand for a simple and practical method in which compounds having —$CF_2O$— as a linking group are purified, without deterioration of the compounds, to thereby increase the purity and resistivity of the compounds. However, specific methods meeting the demand have not been reported yet.

CITATION LIST

Patent Literature

PTL 1: Japanese Unexamined Patent Application Publication No. 62-210420

PTL 2: Japanese Unexamined Patent Application Publication No. 58-1774

SUMMARY OF INVENTION

Technical Problem

Under the above-described circumstances, the present invention has been made. An object of the present invention is to provide a simple and practical method of purifying a compound having —$CF_2O$— as a linking group.

Solution to Problem

Under the above-described circumstances, inventors of the present invention performed thorough studies. As a result, the inventors have found a simple and practical method in which, after synthesis of a compound having —$CF_2O$— as a linking group, by reducing the probability that the compound comes into contact with oxygen, the compound can be treated so as to have a high resistivity without deterioration of the compound. Thus, the present invention has been accomplished.

Specifically, the present invention provides a method for producing a compound represented by general formula (I), the method including sequential steps including preparing a solution of at least one compound represented by general formula (I)

[Chem. 1]

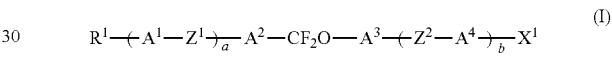

(I)

(in the general formula (I), $R^1$ represents an alkyl group having 1 to 6 carbon atoms, an alkenyl group having 2 to 6 carbon atoms, an alkoxy group having 1 to 6 carbon atoms, or an alkenyloxy group having 2 to 6 carbon atoms, a represents 0, 1, or 2, b represents 0, 1, or 2, and satisfy $0 \leq a+b \leq 3$, $A^1$, $A^2$, $A^3$, and $A^4$ each independently represent a group selected from the group consisting of (a) a trans-1,4-cyclohexylene group (in this group, a single —$CH_2$— or two or more —$CH_2$— that are not next to each other may be replaced by —O— or —S—), (b) a 1,4-phenylene group (in this group, a single —CH= or two or more —CH= that are not next to each other may be replaced by a nitrogen atom), and (c) a 1,4-bicyclo(2.2.2)octylene group, a naphthalene-2,6-diyl group, a decahydronaphthalene-2,6-diyl group, a 1,2,3,4-tetrahydronaphthalene-2,6-diyl group, or a chroman-2,6-diyl group; hydrogen atoms in the group (a), (b), or (c) may be each replaced by a fluorine atom, a trifluoromethyl group, a trifluoromethoxy group, or a chlorine atom; in a case where a represents 2 and a plurality of $A^1$ are present, these plurality of $A^1$ may be the same or different; in a case where b represents 2 and a plurality of $A^4$ are present, these plurality of $A^4$ may be the same or different, $Z^1$ and $Z^2$ each independently represent a single bond, —$CH_2CH_2$—, —CH=CH—, —C≡C—, —$CH_2O$—, —$OCH_2$—, —$CF_2O$—, —$OCF_2$—, —COO—, or —OCO—; in a case where a represents 2 and a plurality of $Z^1$ are present, these plurality of $Z^1$ may be the same or different; in a case where b represents 2 and a plurality of $Z^2$ are present, these plurality of $Z^2$ may be the same or different, and $X^1$ represents a fluoromethoxy group, a difluoromethoxy group, a trifluoromethoxy group, a fluorine atom, a chlorine atom, an alkyl group having 1 to 6 carbon atoms, an alkenyl group having 2 to 6 carbon atoms, an alkoxy group having 1 to 6 carbon atoms, or an alkenyloxy group having 2 to 6 carbon atoms);

bringing the solution into contact with a purifying agent or not bringing the solution into contact with a purifying agent; subsequently performing crystallization from an obtained solution for crystallization to precipitate a crystal; collecting the crystal by filtration; and drying the crystal, wherein steps from initiation of the crystallization step to end of the drying step are performed in an atmosphere having an oxygen concentration of 3% by volume or less.

Advantageous Effects of Invention

According to the present invention, a compound having —$CF_2O$— as a linking group can be purified by a simple and practical method.

DESCRIPTION OF EMBODIMENTS

The present invention provides a method for producing a compound having —$CF_2O$— as a linking group, the method including sequential steps including preparing a solution of a compound having —$CF_2O$— as a linking group, subsequently performing crystallization from the obtained solution for crystallization to precipitate a crystal, collecting the crystal by filtration, and drying the crystal, wherein at least steps from the initiation of the crystallization step to the end of the drying step are performed in an atmosphere having a predetermined low oxygen concentration.

The compound having —$CF_2O$— as a linking group is preferably a compound represented by general formula (I) specifically described below. The solution may contain only a single compound having —$CF_2O$— as a linking group, or two or more of such compounds.

The above-described sequential steps may include, prior to the step (crystallization step) of precipitating a crystal from the solution for crystallization, a step (purifying-agent contact step) of bringing the solution of a compound having —$CF_2O$— as a linking group into contact with a purifying agent; and/or a step (partial-or-entire solvent distillation-removal step) of partially or entirely removing solvent by distillation from the solution of a compound having —$CF_2O$— as a linking group; and/or a step (solvent addition step) of adding solvent to the solution of a compound having —$CF_2O$— as a linking group. Alternatively, these steps may be omitted. In the case where the purifying-agent contact step and the partial-or-entire solvent distillation-removal step are performed, after the purifying-agent contact step is performed, the partial-or-entire solvent distillation-removal step is preferably performed. In the case where the purifying-agent contact step, the partial-or-entire solvent distillation-removal step, and the solvent addition step are performed, after the purifying-agent contact step is performed and then the partial-or-entire solvent distillation-removal step is performed, the solvent addition step is preferably performed.

In the case where the solution of a compound having —$CF_2O$— as a linking group has a low concentration for the purifying-agent contact step, the partial solvent distillation-removal step may be performed before the purifying-agent contact step is performed. The solution to be subjected to the purifying-agent contact step preferably has such a concentration that crystals do not precipitate.

After the crystallization step, the step (crystal filtration-collection step) of collecting the obtained crystal by filtration and the step (crystal drying step) of drying the crystal are performed.

After the crystal drying step, a step (container-packing step) of packing the crystal into a container may be further performed.

The container into which obtained crystals are packed is preferably a container that can be sealed. More preferred is a container formed of a material having low permeability to water vapor and oxygen gas, so that entry of water and oxygen can be shielded. In order to see the content through the container, a transparent container is preferably employed. In order to suppress effects of light such as ultraviolet rays on crystals, an opaque container or a dark-color container is preferably employed. The material for such a container is not particularly limited; and examples of the material include glass, metal, and plastic. The container is preferably packed with, in addition to the obtained crystals, fluid such as gas. Such fluid packed into the container together with the obtained crystals preferably has a low oxygen concentration similar to that of the atmosphere used in the sequential steps. Examples of the fluid include gases having a low oxygen concentration, such as inert gases and gas mixtures of inert gases.

In the present invention, an organic solvent used as a solvent for dissolving a compound having —$CF_2O$— as a linking group is preferably a saturated or aromatic hydrocarbon that has 6 to 9 carbon atoms and does not have a carbon-carbon unsaturated bond except for a benzene ring. For example, this organic solvent may be an alkane, a cycloalkane, an alkyl cycloalkane, benzene, an alkyl benzene, a dialkyl benzene, or the like. Specifically, preferred is a single solvent or a solvent mixture of two or more solvents selected from hexane and structural isomers thereof (acyclic saturated hydrocarbons having 6 carbon atoms), heptane and structural isomers thereof (acyclic saturated hydrocarbons having 7 carbon atoms), octane and structural isomers thereof (acyclic saturated hydrocarbons having 8 carbon atoms), petroleum ether, benzene, toluene, xylene, cumene, methanol, ethanol, 1-propanol, 2-propanol, acetone, 2-butanone, ethyl acetate, diethyl ether, tetrahydrofuran, methyl-t-butyl ether, acetonitrile, and propiononitrile. More preferred is a single solvent or a solvent mixture containing one or two or more solvents selected from hexane and structural isomers thereof, heptane and structural isomers thereof, and toluene.

In the cases of obtaining the solution for crystallization by performing, prior to the crystallization step, at least one of the purifying-agent contact step, the partial-or-entire solvent distillation-removal step, and the solvent addition step, for example, the following methods (1) to (5) may be performed.

(1) First Method

In the first method, the solution of a compound having —$CF_2O$— as a linking group is subjected to the purifying-agent contact step and, from the obtained solution for crystallization, crystals are precipitated.

In the case where the purifying-agent contact step is performed prior to the crystallization step, the purifying agent is preferably silica gel, alumina, ion-exchange resin, or a mixture of the foregoing. Such silica gel or alumina may be chemically modified with a hydrophobic group, a hydrophilic group, a functional group, or the like.

The amount of the purifying agent used with respect to 100 parts by mass of the total amount of compounds having —$CF_2O$— as a linking group is preferably 0.1 parts by mass or more, preferably 0.5 parts by mass or more, preferably 1 part by mass or more, preferably 3 parts by mass or more, preferably 5 parts by mass or more, preferably 10 parts by mass or more, preferably 30 parts by mass or more; preferably 1000 parts by mass or less, preferably 500 parts by mass or less, preferably 300 parts by mass or less, preferably 200 parts by mass or less, preferably 100 parts by mass or less, more preferably 50 parts by mass or less, and may be 10 parts by mass or less.

In this case, the process by which the solution is brought into contact with the purifying agent is not particularly limited; for example, the following process (A) or (B) may be performed.

(A) The solution of a compound having —$CF_2O$— as a linking group is passed through a chromatographic column packed with the purifying agent to provide a solution.

In this process, the amount of the purifying agent used with respect to 100 parts by mass of the total amount of compounds having —$CF_2O$— as a linking group is preferably 10 parts by mass to 300 parts by mass, more preferably 30 parts by mass to 200 parts by mass. After the solution is passed through the chromatographic column, if necessary, an organic solvent may be further passed so that the obtained solution is mixed with the organic solvent.

(B) The solution of a compound having —$CF_2O$— as a linking group is mixed with the purifying agent and stirred for a certain period, and the used purifying agent is removed by filtration to provide a solution.

In this process, the amount of the purifying agent used with respect to 100 parts by mass of the total amount of compounds having —$CF_2O$— as a linking group is preferably 0.1 parts by mass to 100 parts by mass, more preferably 0.5 parts by mass to 50 parts by mass, particularly preferably 0.5 parts by mass to 10 parts by mass.

(2) Second Method

In the second method, the solution of a compound having —$CF_2O$— as a linking group is subjected to the purifying-agent contact step; solvent is added to the obtained solution; and, from the obtained solution for crystallization, crystals are precipitated.

The amount of solvent used during recrystallization is important. This is because, depending on the amount of solvent used, the yield of crystals and the shape of crystals vary. The solution obtained from the purifying-agent contact step may have an excessively low solvent content. Accordingly, solvent is added so that the amount of the solution for crystallization can be adjusted to be an optimal amount for crystallization.

(3) Third Method

In the third method, the solution of a compound having —$CF_2O$— as a linking group is subjected to the purifying-agent contact step; the partial solvent distillation-removal step is performed to partially remove the solvent of the obtained solution by distillation; and, from the obtained solution for crystallization, crystals are precipitated.

The solution obtained from the purifying-agent contact step may have an excessively large amount. Accordingly, the solvent is partially removed by distillation to increase the concentration of the compound having —$CF_2O$— as a linking group. Thus, the amount of the solution for crystallization can be adjusted to be an optimal amount for crystallization.

(4) Fourth Method

In the fourth method, the solution of a compound having —$CF_2O$— as a linking group is subjected to the purifying-agent contact step; the partial solvent distillation-removal step is performed to partially remove the solvent of the obtained solution by distillation; subsequently, solvent is added; and, from the obtained solution for crystallization, crystals are precipitated.

The solution of a compound having —$CF_2O$— as a linking group is dissolved in a solvent having a low conductivity such as toluene (solvent having a high capability of dissolving the compound having —$CF_2O$— as a linking group), and subjected to the purifying-agent contact step and the partial solvent distillation-removal step; subsequently, solvent is newly added to provide a solvent composition having a higher conductivity. As a result, the solution for crystallization can be adjusted so as to have a composition suitable for recrystallization and the yield of crystals can be increased. Solvents having a low conductivity tend to build up static electricity generated by crystallization, stirring, filtration, and the like. However, by adjusting the composition so as to have a higher conductivity, build up of static electricity can be suppressed.

(5) Fifth Method

In the fifth method, the solution of a compound having —$CF_2O$— as a linking group is subjected to the purifying-agent contact step; the entire solvent distillation-removal step is performed to entirely remove the solvent of the obtained solution by distillation; subsequently, solvent is added to the obtained residue; and, from the obtained solution for crystallization, crystals are precipitated.

According to this method, the composition of the solution used in the purifying-agent contact step and the composition of the solution for crystallization used in the crystallization step can be respectively adjusted to optimal compositions in these steps and used.

In the present invention, among the sequential steps, at least steps from the initiation of the crystallization step to the end of the drying step are performed in an atmosphere having a predetermined low oxygen concentration. The predetermined low oxygen concentration is preferably 3% by volume or less and may be 2% by volume or less, or 1% by volume or less. In order to reduce the probability that a solution of a compound having —$CF_2O$— as a linking group comes into contact with oxygen, steps from the initiation of the crystallization step to the end of the container-packing step are preferably performed in an atmosphere having a predetermined low oxygen concentration.

In the case where the sequential steps include the purifying-agent contact step, steps from the initiation of the purifying-agent contact step to the end of the drying step are preferably performed in an atmosphere having a predetermined low oxygen concentration; more preferably, steps from the initiation of the purifying-agent contact step to the end of the container-packing step are performed in an atmosphere having a predetermined low oxygen concentration.

In order to suppress deterioration due to contact with water, the steps performed in an atmosphere having a predetermined low oxygen concentration are preferably performed at a humidity of 15% or less.

The atmosphere having such a humidity and such an oxygen concentration is preferably prepared by purging with an inert gas or reduction of pressure. More preferably, after the pressure is reduced, an inert gas is introduced to increase the reduced pressure to normal pressure. The inert gas is preferably argon or nitrogen. In the case where the atmosphere is subjected to reduction of pressure, the oxygen concentration prior to reduction of pressure is preferably 3% by volume or less. In this case, even when the composition of the atmosphere is not changed during reduction of pressure, the predetermined low oxygen concentration can be maintained. The reduction of the pressure of the atmosphere is preferably performed, for example, during suction on the filtrate exit side of a filter in the crystal filtration-collection step, or during drying of the crystals. In the case where, in the crystal filtration-collection step, pressure is applied on the slurry supply side of a filter, a gas having a low oxygen concentration such as an inert gas or a gas mixture thereof is supplied.

In the reduced-pressure state, a sufficiently low oxygen partial pressure will suffice in some cases though the oxygen concentration is not 3% by volume or less. For example, an oxygen partial pressure corresponding to an oxygen concentration of 3% by volume or less at the atmospheric pressure (101325 Pa) is about 3000 Pa or less. Accordingly, the oxygen partial pressure in the atmosphere is preferably about 3000 Pa or less or may be 2000 Pa or less, or 1000 Pa or less.

Regarding devices used in the sequential steps, all the devices and pipes used during preparation of the solution, contact with a purifying agent, removal of the purifying agent, crystallization, collection of crystals by filtration, drying of crystals, and transfer of solutions or compounds between steps are desirably connected together so as to be isolated from the outside air.

In particular, it is highly preferable to perform steps from the crystal filtration step to the drying step with a dryer having a filtration function. The dryer having a filtration function is preferably a Rosenmund filter-dryer, a PV mixer having a filtration function, or a conical dryer having a filtration function.

The dryer having a filtration function preferably includes a sealable container for housing slurry containing crystals and solution, a filter for filtration for crystals, and a drying unit configured to dry crystals by heating and/or reduction of pressure. The dryer having a filtration function may be equipped with, for example, a mixing impeller configured to stir slurry; a power unit configured to vibrate, rotate, or incline the container; an inlet for slurry; an exit for filtrate; a rinsing unit configured to rinse crystals; a unit configured to collect and discharge obtained crystals; and a temperature adjusting unit by heating, cooling, or the like. The shape of the container is not particularly limited and may be cylindrical, conical, spherical, or the like. The container may be heated by a method in which a heating jacket is provided outside the container to conduct heat into the container; a method in which piping is installed so as to extend from the outside to the inside of the container and a heating medium is passed through the piping; or a method of blowing a high-temperature gas into the container. The drying method may be drying by heating, drying under reduced pressure, vacuum drying, freeze drying, or a combination of two or more thereof. The filter surface may be a surface horizontally disposed in a lower portion or an intermediate portion of the container, or a cylindrical or conical surface conforming to the wall surface of the container. Separation of crystals from the filter surface or movement of crystals for discharge from the container is preferably achieved by, for example, mechanical scraping or pressure applied by gas blasting. In the case where a gas is introduced into the dryer having a filtration function, an inert gas is preferably used in order not to increase the oxygen concentration of the atmosphere within the container.

<Compound Represented by General Formula (I)>

The compound having —$CF_2O$— as a linking group may be a compound represented by general formula (I) below. The solution may contain a single compound represented by the general formula (I) or two or more compounds represented by the general formula (I).

[Chem. 2]

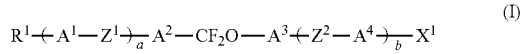

(I)

In the general formula (I), $R^1$ represents an alkyl group having 1 to 6 carbon atoms, an alkenyl group having 2 to 6 carbon atoms, an alkoxy group having 1 to 6 carbon atoms, or an alkenyloxy group having 2 to 6 carbon atoms.

In the general formula (I), a represents 0, 1, or 2, b represents 0, 1, or 2, and satisfy 0≤a+b≤3.

In the general formula (I), $A^1$, $A^2$, $A^3$, and $A^4$ each independently represent a group selected from the group consisting of (a) a trans-1,4-cyclohexylene group (in this group, a single —$CH_2$— or two or more —$CH_2$— that are not next to each other may be replaced by —O— or —S—), (b) a 1,4-phenylene group (in this group, a single —CH= or two or more —CH= that are not next to each other may be replaced by a nitrogen atom), and (c) a 1,4-bicyclo(2.2.2)octylene group, a naphthalene-2,6-diyl group, a decahydronaphthalene-2,6-diyl group, a 1,2,3,4-tetrahydronaphthalene-2,6-diyl group, or a chroman-2,6-diyl group; hydrogen atoms in the group (a), (b), or (c) may be each replaced by a fluorine atom, a trifluoromethyl group, a trifluoromethoxy group, or a chlorine atom.

In a case where a represents 2 and a plurality of $A^1$ are present, these plurality of $A^1$ may be the same or different.

In a case where b represents 2 and a plurality of $A^4$ are present, these plurality of $A^4$ may be the same or different.

$Z^1$ and $Z^2$ each independently represent a single bond, —$CH_2CH_2$—, —CH=CH—, —C≡C—, —$CH_2O$—, —$OCH_2$—, —$CF_2O$—, —$OCF_2$—, —COO—, or —OCO—.

In a case where a represents 2 and a plurality of $Z^1$ are present, these plurality of $Z^1$ may be the same or different.

In a case where b represents 2 and a plurality of $Z^2$ are present, these plurality of $Z^2$ may be the same or different.

$X^1$ represents a fluoromethoxy group, a difluoromethoxy group, a trifluoromethoxy group, a fluorine atom, a chlorine atom, an alkyl group having 1 to 6 carbon atoms, an alkenyl group having 2 to 6 carbon atoms, an alkoxy group having 1 to 6 carbon atoms, or an alkenyloxy group having 2 to 6 carbon atoms.

First Embodiment of Compound Represented by General Formula (I)

The compound represented by the general formula (I) may be a p-type liquid crystal compound in which dielectric anisotropy Δ∈ satisfies Δ∈>0 and the absolute value of Δ∈ is large.

The compound group of this first embodiment includes, for example, a compound represented by the general formula (I) where $R^1$ represents an alkyl group having 1 to 5 carbon atoms or an alkenyl group having 2 to 5 carbon atoms; $A^1$, $A^2$, $A^3$, and $A^4$ each independently represent any one of the following formulae (the left and right of these formulae are the same as the left and right of the general formula (I))

[Chem. 3]

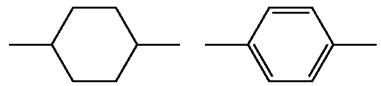

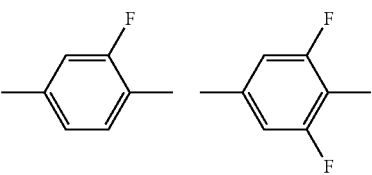

$Z^1$ and $Z^2$ each independently represent a single bond, —$CH_2CH_2$—, or —$CF_2O$—; and $X^1$ represents a trifluoromethoxy group or a fluorine atom.

In the first embodiment, $R^1$ in the general formula (I) preferably represents a linear alkyl group having 1 to 5 carbon atoms or a linear alkenyl group having 2 to 5 carbon atoms.

Specific examples of the compound represented by the general formula (I) in the first embodiment include, but are not particularly limited to, compounds represented by the following general formulae (I-1.1) to (I-1.4) and (I-1.11) to (I-1.16).

[Chem. 4]

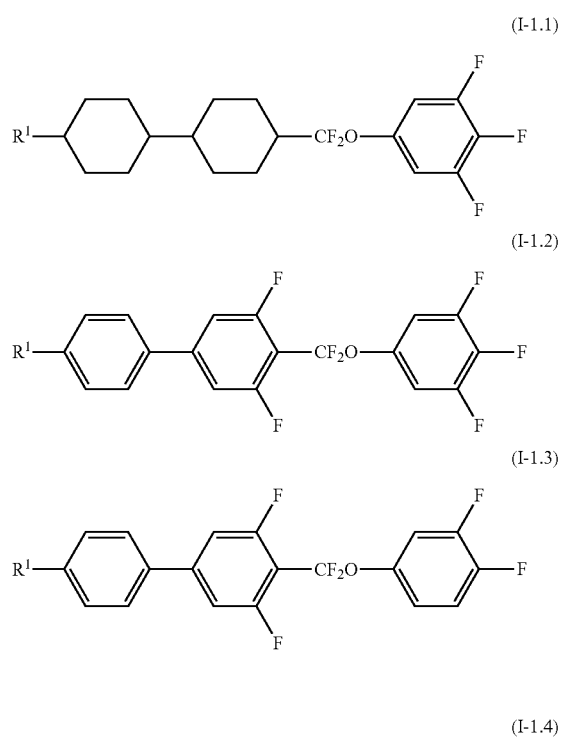

[Chem. 5]

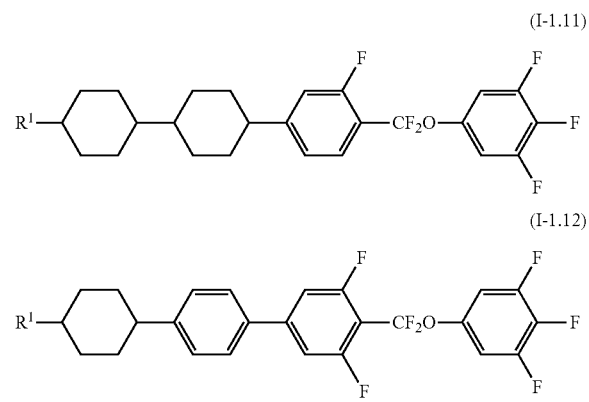

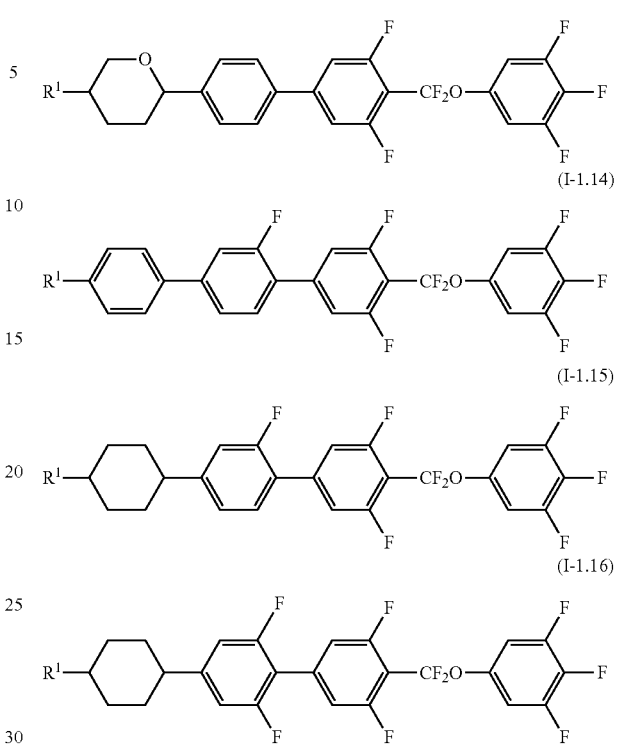

In the general formulae (I-1.1) to (I-1.4) and (I-1.11) to (I-1.16), $R^1$ represents an alkyl group having 1 to 5 carbon atoms or an alkenyl group having 2 to 5 carbon atoms.

Second Embodiment of Compound Represented by General Formula (I)

The compound represented by the general formula (I) may be an n-type liquid crystal compound in which dielectric anisotropy $\Delta\varepsilon$ satisfies $\Delta\varepsilon<0$ and the absolute value of $\Delta\varepsilon$ is large.

The compound group of this second embodiment includes, for example, a compound represented by the general formula (I) where $R^1$ represents an alkyl group having 1 to 5 carbon atoms or an alkenyl group having 2 to 5 carbon atoms; $A^1$, $A^2$, $A^3$, and $A^4$ each independently represent any one of the following formulae (the left and right of these formulae are the same as the left and right of the general formula (I))

[Chem. 6]

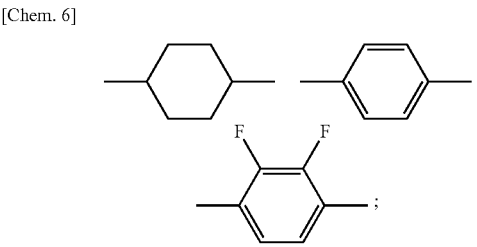

$Z^1$ and $Z^2$ each independently represent a single bond, —$CH_2CH_2$—, or —$CF_2O$—; and $X^1$ represents an alkyl group having 1 to 5 carbon atoms, an alkenyl group having 2 to 5 carbon atoms, an alkoxy group having 1 to 5 carbon atoms, or an alkenyloxy group having 2 to 5 carbon atoms.

In the second embodiment, $R^1$ in the general formula (I) preferably represents a linear alkyl group having 1 to 5 carbon atoms or a linear alkenyl group having 2 to 5 carbon atoms.

In the second embodiment, $X^1$ in the general formula (I) preferably represents a linear alkyl group having 1 to 5 carbon atoms, a linear alkenyl group having 2 to 5 carbon atoms, a linear alkoxy group having 1 to 5 carbon atoms, or a linear alkenyloxy group having 2 to 5 carbon atoms.

Specific examples of the compound represented by the general formula (I) in the second embodiment include, but are not particularly limited to, compounds represented by the following general formulae (I-2.1) to (I-2.18).

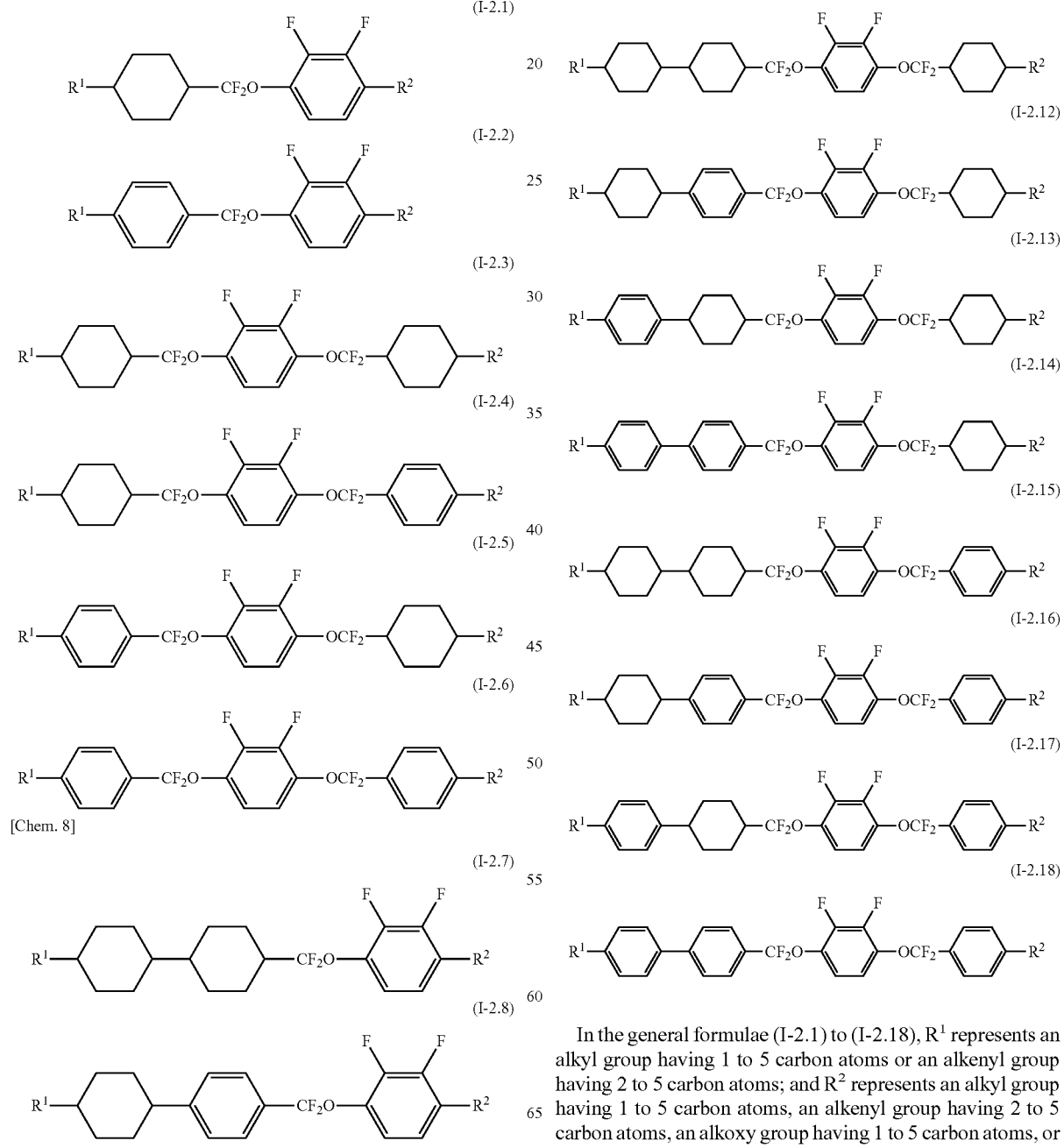
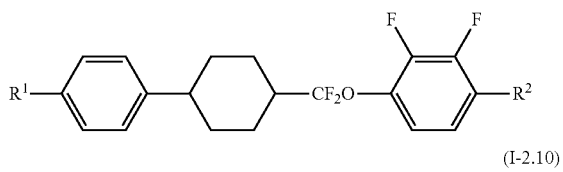
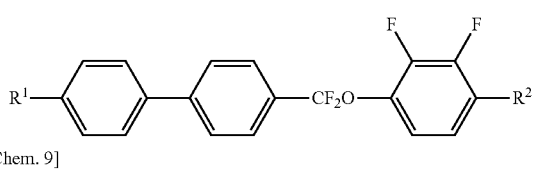

In the general formulae (I-2.1) to (I-2.18), $R^1$ represents an alkyl group having 1 to 5 carbon atoms or an alkenyl group having 2 to 5 carbon atoms; and $R^2$ represents an alkyl group having 1 to 5 carbon atoms, an alkenyl group having 2 to 5 carbon atoms, an alkoxy group having 1 to 5 carbon atoms, or an alkenyloxy group having 2 to 5 carbon atoms.

Third Embodiment of Compound Represented by General Formula (I)

The compound represented by the general formula (I) may be a non-polar liquid crystal compound in which the absolute value of dielectric anisotropy Δ∈ is relatively small.

The compound group of this third embodiment includes, for example, a compound represented by the general formula (I) where $R^1$ represents an alkyl group having 1 to 5 carbon atoms or an alkenyl group having 2 to 5 carbon atoms; $A^1$, $A^2$, $A^3$, and $A^4$ each independently represent any one of the following formulae (the left and right of these formulae are the same as the left and right of the general formula (I))

[Chem. 10]

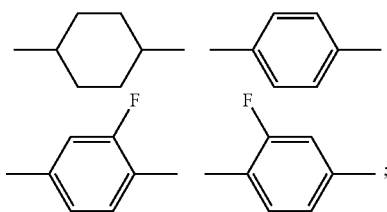

$Z^1$ and $Z^2$ each independently represent a single bond, —CH$_2$CH$_2$—, or —CF$_2$O—; and $X^1$ represents an alkyl group having 1 to 5 carbon atoms or an alkenyl group having 2 to 5 carbon atoms.

In the third embodiment, $R^1$ in the general formula (I) preferably represents a linear alkyl group having 1 to 5 carbon atoms or a linear alkenyl group having 2 to 5 carbon atoms.

In the third embodiment, $X^1$ in the general formula (I) preferably represents a linear alkyl group having 1 to 5 carbon atoms or a linear alkenyl group having 2 to 5 carbon atoms.

Specific examples of the compound represented by the general formula (I) in the third embodiment include, but are not particularly limited to, compounds represented by the following general formulae (I-3.1) to (I-3.8).

[Chem. 11]

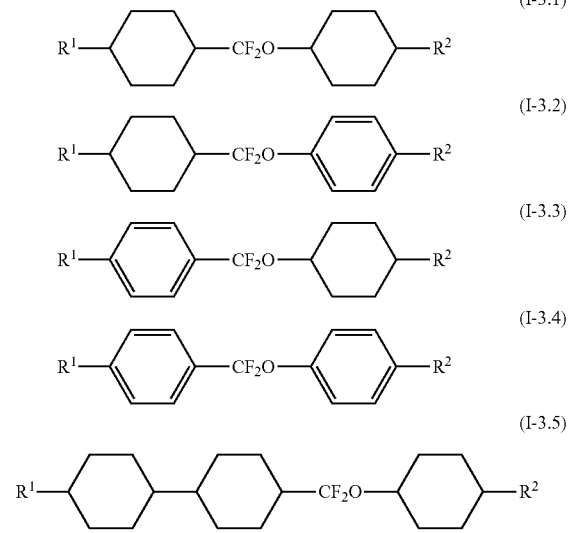

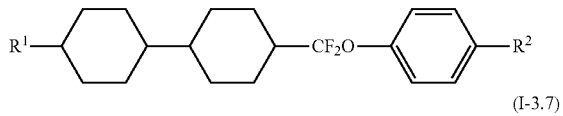

(I-3.6)

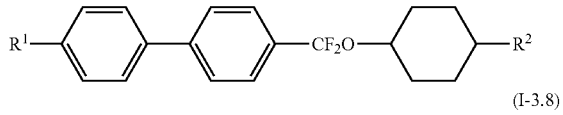

(I-3.7)

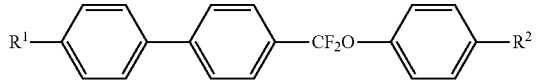

(I-3.8)

In the general formulae (I-3.1) to (I-3.8), $R^1$ represents an alkyl group having 1 to 5 carbon atoms or an alkenyl group having 2 to 5 carbon atoms; and $R^2$ represents an alkyl group having 1 to 5 carbon atoms or an alkenyl group having 2 to 5 carbon atoms.

Regarding a compound represented by the general formula (I) and produced by a production method according to the present invention, an oxidation reaction and the like caused by contact with oxygen, water, and the like during a purification treatment are suppressed and a compound having a high purity and a high resistivity can be obtained. This method is simple and practical and allows reduction in the production cost.

The obtained compound represented by the general formula (I) can be mixed with another compound and used to prepare a liquid crystal material (liquid crystal composition).

Such another compound used as a liquid crystal material is, for example, a compound represented by the following general formula (II).

[Chem. 12]

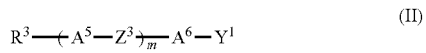

(II)

In the general formula (II), $R^3$ represents a linear alkyl group having 1 to 6 carbon atoms, an alkenyl group having 2 to 6 carbon atoms, an alkoxy group having 1 to 6 carbon atoms, or an alkenyloxy group having 2 to 6 carbon atoms. $R^3$ preferably represents a linear alkyl group having 1 to 6 carbon atoms, a linear alkenyl group having 2 to 6 carbon atoms, a linear alkoxy group having 1 to 6 carbon atoms, or a linear alkenyloxy group having 2 to 6 carbon atoms.

In the general formula (II), m represents 1, 2, or 3; $A^5$ and $A^6$ each independently represent a group selected from the group consisting of (a) a trans-1,4-cyclohexylene group (in this group, a single —CH$_2$— or two or more —CH$_2$— that are not next to each other may be replaced by —O— or —S—), (b) a 1,4-phenylene group (in this group, a single —CH= or two or more —CH= that are not next to each other may be replaced by —N=), and (c) a 1,4-bicyclo(2.2.2)octylene group, a naphthalene-2,6-diyl group, a decahydronaphthalene-2,6-diyl group, a 1,2,3,4-tetrahydronaphthalene-2,6-diyl group, or a chroman-2,6-diyl group; one or two or more hydrogen atoms in the group (a), (b), or (c) may be each replaced by a fluorine atom, a trifluoromethyl group, a trifluoromethoxy group, or a chlorine atom; in a case where m represents 2 or 3 and a plurality of $A^5$ are present, these plurality of $A^5$ may be the same or different.

In the general formula (II), $Z^3$ represents a single bond, —CH$_2$CH$_2$—, —CH=CH—, —C≡C—, —CH$_2$O—, —OCH$_2$—, —CF$_2$O—, —OCF$_2$—, —COO—, or —OCO—; in a case where m represents 2 or 3 and a plurality of $Z^3$ are present, these plurality of $Z^3$ may be the same or different.

In the general formula (II), $Y^1$ represents a hydrogen atom, a fluorine atom, a chlorine atom, a trifluoromethyl group, a trifluoromethoxy group, an alkyl group having 1 to 6 carbon atoms, an alkenyl group having 2 to 6 carbon atoms, an alkoxy group having 1 to 6 carbon atoms, or an alkenyloxy group having 2 to 6 carbon atoms.

A polymerizable compound may also be used as a liquid crystal material. For example, a polymerizable compound represented by the following general formula (III) may be used.

[Chem. 13]

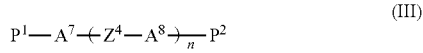

(III)

In the general formula (III), $P^1$ and $P^2$ each independently represent an acryloyloxy group, a methacryloyloxy group, a vinyl group, a vinyloxy group, or a monovalent group represented by any one of the following formulae (Ep-1) to (Ep-7).

[Chem. 14]

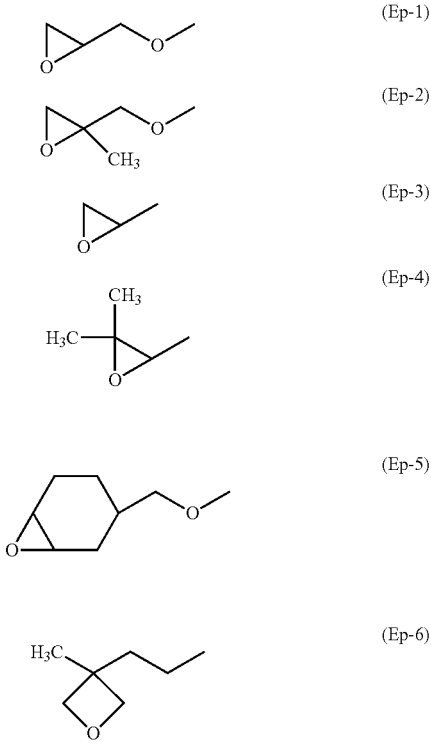

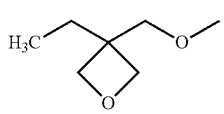

(Ep-7)

Each of the groups represented by the formulae (Ep-1) to (Ep-7) forms a bond at the upper-right bonding end. For example, (Ep-1) represents a glycidyloxy group and (Ep-3) represents an oxiranyl group.

In the general formula (III), n represents 0, 1, or 2, $A^7$ and $A^8$ each independently represent a 1,4-phenylene group or a naphthalene-2,6-diyl group (one or two or more hydrogen atoms in these groups may be each replaced by a fluorine atom); and, in a case where n represents 2 and a plurality of $A^8$ are present, these plurality of $A^8$ may be the same or different.

$Z^4$ represents —COO—, —OCO—, or a single bond; and, in a case where n represents 2 and a plurality of $Z^4$ are present, these plurality of $Z^4$ may be the same or different.

Compounds used in the present invention preferably do not have any peroxide (—OO— or —OO—OO—) moiety such as peracid within the molecule; that is, oxygen atoms are preferably not directly next to each other. In a case where the reliability and long-term stability of the liquid crystal composition are priorities, compounds having a carbonyl group are preferably not used. In a case where stability upon irradiation with UV is a priority, compounds substituted with chlorine atoms are desirably not used.

A liquid crystal composition according to the present invention may contain a polymerizable compound for the purpose of producing a liquid crystal display device employing the polymer stabilized (PS) mode, the polymer sustained alignment (PSA) mode, the transverse-electric-field-type PSVA (polymer stabilized vertical alignment) mode, or the like. Usable polymerizable compounds are, for example, photopolymerizable monomers that undergo polymerization with energy rays such as light. Regarding the structure, for example, such polymerizable compounds may have a liquid crystal skeleton in which a plurality of six-membered rings are combined, such as biphenyl derivatives or terphenyl derivatives.

In a case where a monomer is added to a liquid crystal composition according to the present invention, polymerization proceeds in the absence of a polymerization initiator. However, in order to promote polymerization, the liquid crystal composition may contain a polymerization initiator. Examples of the polymerization initiator include benzoin ethers, benzophenones, acetophenones, benzyl ketals, and acylphosphine oxides.

In a liquid crystal composition containing a polymerizable compound according to the present invention, the polymerizable compound contained therein is polymerized upon irradiation with ultraviolet rays to thereby provide a liquid crystal alignment capability. Thus, the liquid crystal composition is used in liquid crystal display devices in which birefringence of the liquid crystal composition is used to control the amount of light transmission. The composition is useful for AM-LCDs (active matrix liquid crystal display devices), TNs (twisted nematic liquid crystal display devices), STN-LCDs (super twisted nematic liquid crystal display devices), OCB-LCDs, IPS-LCDs (in-plane switching liquid crystal display devices), and FFSs (fringe field switching mode liquid crystal display devices). In particular, the composition is useful for AM-LCDs having active matrix addressing units and is applicable to transmissive or reflective liquid crystal display devices.

Two substrates of a liquid crystal cell used for a liquid crystal display device may be formed of a flexible transparent material such as glass or plastic; one of the substrates may be formed of an opaque material such as silicone. A transparent substrate having a transparent electrode layer can be obtained by, for example, sputtering of indium tin oxide (ITO) onto a transparent substrate such as a glass plate.

Color filters can be formed by, for example, a pigment dispersion process, a printing process, an electrodeposition process, or a dyeing process. A process of forming a color filter by the pigment dispersion process is described as an example: a curable colored material for the color filter is applied to the transparent substrate, subjected to a patterning treatment, and cured by heating or irradiation with light. This step is performed for three colors of red, green, and blue, so that pixel portions for color filters can be formed. In addition, on the substrate, pixel electrodes may be disposed that are equipped with active elements such as TFTs, thin-film diodes, or metal insulator metal resistivity elements.

The substrates are disposed so as to oppose each other with the transparent electrode layer therebetween. At this time, a spacer may be interposed to adjust the distance between the substrates. This adjustment is preferably performed such that the resultant light control layer has a thickness of 1 to 100 µm. The thickness is more preferably 1.5 to 10 µm. In a case where a polarizing plate is used, the product of liquid crystal refractive index anisotropy Δn and cell thickness d is preferably adjusted such that the contrast is maximized. In a case where two polarizing plates are present, the polarizing axis of each polarizing plate may be adjusted to enhance viewing angle or contrast. In addition, in order to increase the viewing angle, a phase difference film may be used. The spacer may be, for example, a columnar spacer formed of glass particles, plastic particles, alumina particles, a photoresist material, or the like. After that, a sealing agent such as an epoxy-based thermosetting composition or the like is applied to the substrates by screen printing so as to form a liquid crystal inlet. The substrates are bonded together and heated to thermally cure the sealing agent.

A process of sandwiching a polymerizable-compound-containing liquid crystal composition between two substrates may be a standard vacuum injection process, a one drop fill (ODF) process, or the like. In the vacuum injection process, dropping marks are not formed; however, injection marks are disadvantageously left. The present invention is more suitably applicable to display devices that are produced by the ODF process. In a step of producing a liquid crystal display device by the ODF process, a sealing agent such as an epoxy-based agent curable by light and heat is applied to one of substrates, that is, the backplane or the frontplane, with a dispenser so as to draw a closed loop wall; within the loop, a predetermined amount of the liquid crystal composition is dropped in a degassed state; and, after that, the frontplane and the backplane are bonded together to thereby produce a liquid crystal display device. A liquid crystal composition according to the present invention allows stable dropping of the liquid crystal composition in the ODF step and hence can be suitably used.

Regarding a process of polymerizing the polymerizable compound, an appropriate rate of polymerization is desirable to achieve good liquid crystal alignment performance. Accordingly, preferred is a polymerization process of applying an active energy ray, such as an ultraviolet ray or an electron beam, alone, or applying active energy rays in combination or in sequence. In the case where an ultraviolet ray is used, a polarized light source may be used or a non-polarized light source may be used. In the case where polymerization is caused in a polymerizable-compound-containing liquid crystal composition sandwiched between two substrates, at least a substrate to be irradiated needs to have appropriate transparency to the active energy ray. The following process may be used: polymerization is caused in predetermined regions alone by using a mask during application of light; after that, conditions in terms of an electric field, a magnetic field, temperature, or the like are changed so that the alignment state of unpolymerized regions is changed; and an active energy ray is further applied to cause polymerization. In particular, in the case of exposure to ultraviolet rays, exposure to ultraviolet rays is preferably performed while an alternating electric field is applied to the polymerizable-compound-containing liquid crystal composition. Regarding the applied alternating electric field, the alternating current preferably has a frequency of 10 Hz to 10 kHz, more preferably, a frequency of 60 Hz to 10 kHz; and the voltage is selected depending on the desired pretilt angle of the liquid crystal display device. That is, the applied voltage can be used to control the pretilt angle of the liquid crystal display device. In a liquid crystal display device employing the transverse-electric-field-type MVA mode, the pretilt angle is preferably controlled in the range of 80° to 89.9° from the viewpoint of alignment stability and contrast.

The temperature during irradiation is preferably within such a temperature range that the liquid crystal state of a liquid crystal composition according to the present invention is maintained. Polymerization is preferably caused at about room temperature, that is, typically 15° C. to 35° C. A lamp that generates ultraviolet rays may be a metal halide lamp, a high-pressure mercury-vapor lamp, an ultra-high-pressure mercury-vapor lamp, or the like. The wavelength of an ultraviolet ray applied is preferably in a wavelength region that does not correspond to the absorption wavelength region of the liquid crystal composition; and, if necessary, an ultraviolet ray is preferably filtered and used. The intensity of the ultraviolet ray applied is preferably 0.1 mW/cm$^2$ to 100 W/cm$^2$, more preferably 2 mW/cm$^2$ to 50 W/cm$^2$. The amount of energy of the ultraviolet ray applied can be appropriately adjusted and is preferably 10 mJ/cm$^2$ to 500 J/cm$^2$, more preferably 100 mJ/cm$^2$ to 200 J/cm$^2$. During application of the ultraviolet ray, the intensity thereof may be varied. The time for applying the ultraviolet ray is appropriately selected depending on the intensity of the applied ultraviolet ray and is preferably 10 seconds to 3600 seconds, more preferably 10 seconds to 600 seconds.

A liquid crystal display device including a liquid crystal composition according to the present invention is advantageous in that high-speed response and suppression of display failure are both achieved. In particular, a liquid crystal composition according to the present invention is useful for active-matrix-driving liquid crystal display devices and is applicable to liquid crystal display devices employing the VA mode, the PSVA mode, the PSA mode, the IPS mode, the FFS mode, or the ECB mode.

EXAMPLES

Hereinafter, the present invention will be described further in detail with reference to Examples. However, the present invention is not limited to these Examples. Regarding compositions of Examples and Comparative examples below, "%" denotes "% by mass". The purity was calculated from an area ratio obtained by gas chromatography (column: DB-1, carrier gas: helium).

Example 1

A compound (100 g, purity: 99.90%) represented by the following formula (1-1)

[Chem. 15]

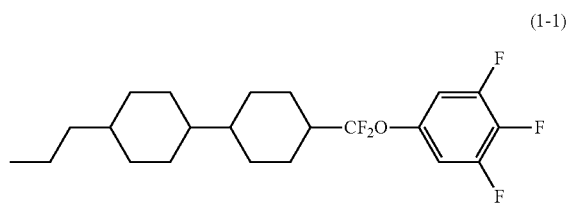

(1-1)

was dissolved in 400 mL of hexane. A chromatographic column (packed with 50 g of silica gel serving as a purifying agent) was prepared. The bottom of the chromatographic column was connected to a sealed container having been purged with argon three times and equipped with a balloon filled with argon. The solution prepared above was poured into the chromatographic column until the surface of the solution reached the upper surface of the purifying agent layer. Furthermore, 300 mL of hexane was added as a developing solvent to elute the compound adsorbed on the purifying agent. Within the sealed container, the oxygen concentration was 3% by volume, the temperature was 20° C., and the humidity was 6%. While the sealing state was maintained, the solution was stirred at −10° C. for 3 hours to cause crystallization. The sealed container was moved into a glove box in which the oxygen concentration was 3% by volume, the temperature was 20° C., and the humidity was 7%; and, within the glove box, crystals were collected by filtration. The crystals were moved into a flask for drying and the flask was attached to a dryer; and the crystals were dried at 133 Pa and at 40° C. for 5 hours. The reduced pressure was increased to normal pressure with argon gas. The obtained compound (82 g) represented by the formula (1-1) was measured in terms of purity and the purity was found to be 99.92%. The obtained compound represented by the formula (1-1) was added, in a ratio of 20%, to a composition having a resistivity of $1.0 \times 10^{13}$ Ω·m and represented by the following formula (1-2).

[Chem. 16]

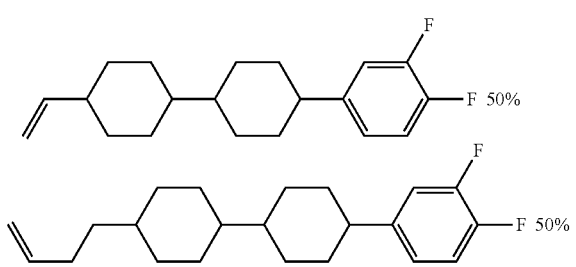

(1-2)

The resultant liquid crystal composition had a resistivity of $2.0 \times 10^{12}$ Ω·m. A liquid crystal display device was produced with the obtained liquid crystal composition. This liquid crystal display device did not cause any display failure and exhibited good characteristics.

The above-described results indicate that this purification method can provide the compound represented by the formula (1-1) and having a high purity and a high resistivity without deterioration.

Example 2

The compound (100 g, purity: 99.90%) represented by the formula (1-1) was dissolved in 400 mL of hexane. To this solution, 1 g of silica gel was added; the container was purged with argon three times and then equipped with a balloon filled with argon. Within the container, the oxygen concentration was 3% by volume, the temperature was 20° C., and the humidity was 6%. This mixture was stirred at room temperature for an hour. After that, filtration was performed within a glove box in which the oxygen concentration was 3% by volume, the temperature was 20° C., and the humidity was 7%. The resultant solution was stirred at −10° C. for 3 hours to cause crystallization. Within the glove box in which the oxygen concentration was 3% by volume, the temperature was 20° C., and the humidity was 7%, crystals were collected by filtration. The crystals were moved into a flask for drying and the flask was attached to a dryer; and the crystals were dried at 133 Pa and at 40° C. for 5 hours. The reduced pressure was increased to normal pressure with argon gas. The obtained compound (83 g) represented by the formula (1-1) was measured in terms of purity and the purity was found to be 99.91%. The obtained compound represented by the formula (1-1) was added, in a ratio of 20%, to a composition having a resistivity of $1.0 \times 10^{13}$ Ω·m and represented by the formula (1-2). The resultant liquid crystal composition had a resistivity of $1.8 \times 10^{12}$ Ω·m. A liquid crystal display device was produced with the obtained liquid crystal composition. This liquid crystal display device did not cause any display failure and exhibited good characteristics.

The above-described results indicate that this purification method can provide the compound represented by the formula (1-1) and having a high purity and a high resistivity without deterioration.

Example 3

The same procedures were performed as in Example 1 except that the compound represented by the formula (1-1) was replaced with a compound (purity: 99.91%) represented by the following formula (1-4).

[Chem. 17]

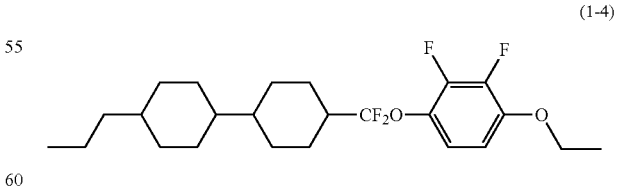

(1-4)

The obtained compound represented by the formula (1-4) was found to have a yield of 83 g and a purity of 99.93%. In addition, the obtained compound represented by the formula (1-4) was added, in a ratio of 20%, to a composition having a resistivity of $1.0 \times 10^{13}$ Ω·m and represented by the formula (1-2). The resultant liquid crystal composition had a resistivity of $1.6 \times 10^{12}$ Ω·m. A liquid crystal display device was produced with the obtained liquid crystal composition. This liquid crystal display device did not cause any display failure and exhibited good characteristics.

The above-described results indicate that this purification method can provide the compound represented by the formula (1-4) and having a high purity and a high resistivity without deterioration.

Example 4

In Example 1, instead of the compound represented by the formula (1-1), a compound (100 g, purity: 99.89%) represented by the following formula (1-5)

[Chem. 18]

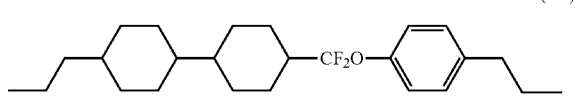

(1-5)

was dissolved in 400 mL of hexane. A chromatographic column (packed with 50 g of silica gel serving as a purifying agent) was prepared. The bottom of the chromatographic column was connected to a sealed container having been purged with argon three times and equipped with a balloon filled with argon. The solution prepared above was poured into the chromatographic column until the surface of the solution reached the upper surface of the purifying agent layer. Furthermore, 300 mL of hexane was added as a developing solvent to elute the compound adsorbed on the purifying agent. Within the sealed container, the oxygen concentration was 3% by volume, the temperature was 20° C., and the humidity was 6%. From the resultant solution, 400 mL of hexane was distilled off under a reduced pressure. The reduced pressure was increased to normal pressure with argon. The resultant solution was stirred at −20° C. for 3 hours to cause crystallization. The sealed container was moved into a glove box in which the oxygen concentration was 3% by volume, the temperature was 20° C., and the humidity was 7%; and, within the glove box, crystals were collected by filtration. The crystals were moved into a flask for drying and the flask was attached to a dryer; and the crystals were dried at 133 Pa and at 40° C. for 5 hours. The reduced pressure was increased to normal pressure with argon gas. The obtained compound (75 g) represented by the formula (1-5) was measured in terms of purity and the purity was found to be 99.90%. The obtained compound represented by the formula (1-5) was added, in a ratio of 20%, to a composition having a resistivity of $1.0 \times 10^{13}$ Ω·m and represented by the formula (1-2). The resultant liquid crystal composition had a resistivity of $8.6 \times 10^{12}$ Ω·m. A liquid crystal display device was produced with the obtained liquid crystal composition. This liquid crystal display device did not cause any display failure and exhibited good characteristics.

The above-described results indicate that this purification method can provide the compound represented by the formula (1-5) and having a high purity and a high resistivity without deterioration.

Example 5

The compound (100 g, purity: 99.90%) represented by the formula (1-1) was dissolved in 400 mL of hexane. A chromatographic column (packed with 50 g of silica gel serving as a purifying agent) was prepared. The bottom of the chromatographic column was connected to a sealed container having been purged with argon three times and equipped with a balloon filled with argon. The solution prepared above was poured into the chromatographic column until the surface of the solution reached the upper surface of the purifying agent layer. Furthermore, 300 mL of hexane was added as a developing solvent to elute the compound adsorbed on the purifying agent. From the resultant solution, the solvent was distilled off under a reduced pressure. To the resultant residue (98 g), 300 mL of acetone for electronic materials was added; purging with argon was performed three times; and, after that, the residue was dissolved by heating. Within the container, the oxygen concentration was 3% by volume, the temperature was 23° C., and the humidity was 6%. While the sealing state was maintained, the solution was stirred at −10° C. for 3 hours to cause crystallization. The sealed container was moved into a glove box in which the oxygen concentration was 3% by volume, the temperature was 20° C., and the humidity was 7%; and, within the glove box, crystals were collected by filtration. The crystals were moved into a flask for drying and the flask was attached to a dryer; and the crystals were dried at 133 Pa and at 40° C. for 5 hours. The reduced pressure was increased to normal pressure with argon gas. The obtained compound (90 g) represented by the formula (1-1) was measured in terms of purity and the purity was found to be 99.92%. The obtained compound represented by the formula (1-1) was added, in a ratio of 20%, to a composition having a resistivity of $1.0 \times 10^{13}$ Ω·m and represented by the formula (1-2). The resultant liquid crystal composition had a resistivity of $1.2 \times 10^{12}$ Ω·m. A liquid crystal display device was produced with the obtained liquid crystal composition. This liquid crystal display device did not cause any display failure and exhibited good characteristics.

The above-described results indicate that this purification method can provide the compound represented by the formula (1-1) and having a high purity and a high resistivity without deterioration.

Comparative Example 1

The compound (100 g, purity: 99.90%) represented by the formula (1-1) was dissolved in 400 mL of hexane. A chromatographic column (packed with 50 g of silica gel serving as a purifying agent) was prepared. The bottom of the chromatographic column was connected to a sealed container equipped with a balloon. This system was a sealed system but was not purged with an inert gas. The solution prepared above was poured into the chromatographic column until the surface of the solution reached the upper surface of the purifying agent layer. Furthermore, 300 mL of hexane was added as a developing solvent to elute the compound adsorbed on the purifying agent. Within the sealed container, the oxygen concentration was 21% by volume and the humidity was 23%. While the sealing state was maintained, the solution was stirred at −10° C. for 3 hours to cause crystallization. After that, crystals were collected by filtration in the air having an oxygen concentration of 21% by volume and a humidity of 23%. The crystals were moved into a flask for drying and the flask was attached to a dryer; and the crystals were dried at 133 Pa and at 40° C. for 5 hours. The reduced pressure was increased to normal pressure with the air. The obtained compound (82 g) represented by the formula (1-1) was measured in terms of purity and the purity was found to be 99.79%. As a result of analysis, 0.080% of an impurity was newly detected that was a compound represented by the following (1-3)

[Chem. 19]

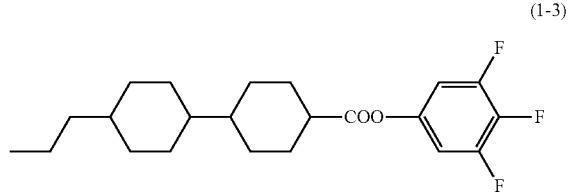

(1-3)

(where —CF$_2$O— in the formula (1-1) is replaced by —COO—). The obtained compound represented by the formula (1-1) was added, in a ratio of 20%, to a composition having a resistivity of 1.0×10$^{13}$ Ω·m and represented by the formula (1-2). The resultant liquid crystal composition had a resistivity of 1.2×10$^{11}$ Ω·m.

These results indicate that the purification method of this Comparative example provides the compound represented by the formula (1-1) and having a low purity and an insufficient resistivity.

Comparative Example 2

The compound (100 g, purity: 99.90%) represented by the formula (1-1) was dissolved in 400 mL of hexane. A chromatographic column (packed with 50 g of silica gel serving as a purifying agent) was prepared. The bottom of the chromatographic column was connected to a sealed container equipped with a balloon. The sealed container was purged with argon gas once. The solution prepared above was poured into the chromatographic column until the surface of the solution reached the upper surface of the purifying agent layer. Furthermore, 300 mL of hexane was added as a developing solvent to elute the compound adsorbed on the purifying agent. Within the sealed container, the oxygen concentration was 5% by volume and the humidity was 10%. While the sealing state was maintained, the solution was stirred at −10° C. for 3 hours to cause crystallization. After that, crystals were collected by filtration within a glove box in which the oxygen concentration was 5% by volume and the humidity was 10%. The crystals were moved into a flask for drying and the flask was attached to a dryer; and the crystals were dried at 133 Pa and at 40° C. for 5 hours. The reduced pressure was increased to normal pressure with argon gas. The obtained compound (82 g) represented by the formula (1-1) was measured in terms of purity and the purity was found to be 99.88%. As a result of analysis, 0.015% of an impurity was newly detected that was a compound represented by the (1-3) (where —CF$_2$O— in the formula (1-1) is replaced by —COO—). The obtained compound represented by the formula (1-1) was added, in a ratio of 20%, to a composition having a resistivity of 1.0×10$^{13}$ Ω·m and represented by the formula (1-2). The resultant liquid crystal composition had a resistivity of 8.2×10$^{11}$ Ω·m.

These results indicate that the purification method of this Comparative example provides the compound represented by the formula (1-1) and having a low purity and an insufficient resistivity.

INDUSTRIAL APPLICABILITY

The present invention is applicable to production of compounds having —CF$_2$O— as a linking group.

The invention claimed is:

1. A method for producing a compound represented by general formula (I), the method comprising sequential steps including
preparing a solution of at least one compound represented by general formula (I)

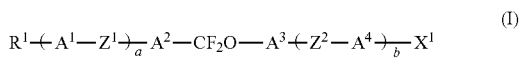

(I)

(in the general formula (I), R$^1$ represents an alkyl group having 1 to 6 carbon atoms, an alkenyl group having 2 to 6 carbon atoms, an alkoxy group having 1 to 6 carbon atoms, or an alkenyloxy group having 2 to 6 carbon atoms,
a represents 0, 1, or 2, b represents 0, 1, or 2, and satisfy 0≤a+b≤3,
A$^1$, A$^2$, A$^3$, and A$^4$ each independently represent a group selected from the group consisting of
(a) a trans-1,4-cyclohexylene group (in this group, a single —CH$_2$— or two or more —CH$_2$— that are not next to each other may be replaced by —O— or —S—),
(b) a 1,4-phenylene group (in this group, a single —CH═ or two or more —CH═ that are not next to each other may be replaced by a nitrogen atom), and
(c) a 1,4-bicyclo(2.2.2)octylene group, a naphthalene-2,6-diyl group, a decahydronaphthalene-2,6-diyl group, a 1,2,3,4-tetrahydronaphthalene-2,6-diyl group, or a chroman-2,6-diyl group; hydrogen atoms in the group (a), (b), or (c) may be each replaced by a fluorine atom, a trifluoromethyl group, a trifluoromethoxy group, or a chlorine atom; in a case where a represents 2 and a plurality of A$^1$ are present, these plurality of A$^1$ may be the same or different; in a case where b represents 2 and a plurality of A$^4$ are present, these plurality of A$^4$ may be the same or different,
Z$^1$ and Z$^2$ each independently represent a single bond, —CH$_2$CH$_2$—, —CH═CH—, —C≡C—, —CH$_2$O—, —OCH$_2$—, —CF$_2$O—, —OCF$_2$—, —COO—, or —OCO—; in a case where a represents 2 and a plurality of Z$^1$ are present, these plurality of Z$^1$ may be the same or different; in a case where b represents 2 and a plurality of Z$^2$ are present, these plurality of Z$^2$ may be the same or different, and
X$^1$ represents a fluoromethoxy group, a difluoromethoxy group, a trifluoromethoxy group, a fluorine atom, a chlorine atom, an alkyl group having 1 to 6 carbon atoms, an alkenyl group having 2 to 6 carbon atoms, an alkoxy group having 1 to 6 carbon atoms, or an alkenyloxy group having 2 to 6 carbon atoms);
bringing the solution into contact with a purifying agent or not bringing the solution into contact with a purifying agent; subsequently performing crystallization from an obtained solution for crystallization to precipitate a crystal; collecting the crystal by filtration; and drying the crystal,
wherein steps from initiation of the crystallization step to end of the drying step are performed in an atmosphere having an oxygen concentration of 3% by volume or less.

2. The method for producing a compound according to claim 1, wherein, after the solution is brought into contact with the purifying agent to provide a solution, solvent is partially removed by distillation from this solution to provide the solution for crystallization.

3. The method for producing a compound according to claim 1, wherein, after the solution is brought into contact with the purifying agent to provide a solution, solvent is partially or entirely removed by distillation from this solution; and, to a solution provided by the partial removal of the solvent or a residue provided by the entire removal of the solvent, solvent is added to provide the solution for crystallization.

4. The method for producing a compound according to claim 1, wherein, after the solution is brought into contact with the purifying agent to provide a purified solution, the solution for crystallization is provided with or without addition of solvent to the purified solution.

5. The method for producing a compound according to claim 1, wherein, in the sequential steps including bringing the solution into contact with the purifying agent, subsequently performing crystallization from the obtained solution for crystallization to precipitate the crystal, collecting the crystal by filtration, and drying the crystal, steps from initiation of the purifying-agent contact step to end of the drying step are performed in an atmosphere having an oxygen concentration of 3% by volume or less.

6. The method for producing a compound according to claim 1, wherein, in the sequential steps including bringing the solution into contact with the purifying agent or not bringing the solution into contact with the purifying agent, subsequently performing crystallization from the obtained solution for crystallization to precipitate the crystal, collecting the crystal by filtration, drying the crystal, and packing the crystal into a container, steps from initiation of the crystallization step to end of the container-packing step are performed in an atmosphere having an oxygen concentration of 3% by volume or less.

7. The method for producing a compound according to claim 1, wherein, in the sequential steps including bringing the solution into contact with the purifying agent, subsequently performing crystallization from the obtained solution for crystallization to precipitate the crystal, collecting the crystal by filtration, drying the crystal, and packing the crystal into a container, steps from initiation of the purifying-agent contact step to end of the container-packing step are performed in an atmosphere having an oxygen concentration of 3% by volume or less.

8. The method for producing a compound according to claim 1, wherein the steps performed in an atmosphere having an oxygen concentration of 3% by volume or less are performed in an atmosphere having an oxygen concentration of 3% by volume or less and a humidity of 15% or less.

9. The method for producing a compound according to claim 1, wherein, in the general formula (I), $R^1$ represents a linear alkyl group having 1 to 5 carbon atoms or a linear alkenyl group having 2 to 5 carbon atoms; $A^1, A^2, A^3$, and $A^4$ each independently represent any one of

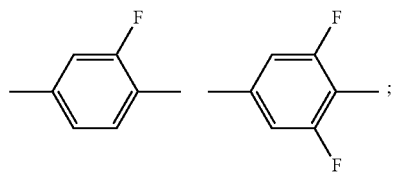

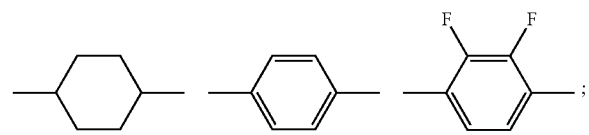

$Z^1$ and $Z^2$ each independently represent a single bond, —$CH_2CH_2$—, or —$CF_2O$—; and $X^1$ represents a trifluoromethoxy group or a fluorine atom.

10. The method for producing a compound according to claim 1, wherein, in the general formula (I), $R^1$ represents a linear alkyl group having 1 to 5 carbon atoms or a linear alkenyl group having 2 to 5 carbon atoms; $A^1, A^2, A^3$, and $A^4$ each independently represent any one of

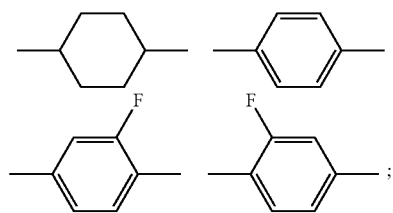

$Z^1$ and $Z^2$ each independently represent a single bond, —$CH_2CH_2$—, or —$CF_2O$—; and $X^1$ represents a linear alkyl group having 1 to 5 carbon atoms, a linear alkenyl group having 2 to 5 carbon atoms, a linear alkoxy group having 1 to 5 carbon atoms, or a linear alkenyloxy group having 2 to 5 carbon atoms.

11. The method for producing a compound according to claim 1, wherein, in the general formula (I), $R^1$ represents a linear alkyl group having 1 to 5 carbon atoms or a linear alkenyl group having 2 to 5 carbon atoms; $A^1, A^2, A^3$, and $A^4$ each independently represent any one of $Z^1$ and $Z^2$ each independently represent a single bond, —$CH_2CH_2$—, or —$CF_2O$—; and $X^1$ represents a linear alkyl group having 1 to 5 carbon atoms or a linear alkenyl group having 2 to 5 carbon atoms.

12. The method for producing a compound according to claim 1, wherein steps from the crystal filtration-collection step to the drying step are performed with a dryer having a filtration function.

13. A method for producing a liquid crystal composition, the method comprising:

providing said at least one compound represented by general formula (I) produced by the method of claim 1; and mixing said at least one compound represented by general formula (I) with at least one other compound than said at least one compound represented by general formula (I).

14. A method for producing a liquid crystal composition, the method comprising:
   providing at least two of said compound represented by general formula (I) produced by the method of claim 1; and
   mixing said at least two with each other.

* * * * *